(12) United States Patent
Dragovich et al.

(10) Patent No.: US 8,442,301 B2
(45) Date of Patent: May 14, 2013

(54) NONDESTRUCTIVE INSPECTION METHOD AND SYSTEM

(75) Inventors: Matthew Edward Dragovich, West Chester, OH (US); Patrick Joseph Howard, Cincinnati, OH (US); Joshua Brian Jamison, Liberty Township, OH (US); Toby George Darkins, Jr., Loveland, OH (US); Joseph Manuel Portaz, Hamilton, OH (US)

(73) Assignee: General Electric Company, Schenectady, NY (US)

( * ) Notice: Subject to any disclaimer, the term of this patent is extended or adjusted under 35 U.S.C. 154(b) by 429 days.

(21) Appl. No.: 12/433,168

(22) Filed: Apr. 30, 2009

(65) Prior Publication Data
US 2010/0278440 A1 Nov. 4, 2010

(51) Int. Cl.
*G06K 9/00* (2006.01)
(52) U.S. Cl.
USPC .......................................................... 382/152
(58) Field of Classification Search .................. 382/141, 382/143, 152; 356/479, 497, 394, 448
See application file for complete search history.

(56) References Cited

U.S. PATENT DOCUMENTS

| | | | |
|---|---|---|---|
| 4,878,169 A * | 10/1989 | Toner et al. | 382/131 |
| 5,015,540 A | 5/1991 | Borom et al. | |
| 5,330,854 A | 7/1994 | Singh et al. | |
| 5,336,350 A | 8/1994 | Singh | |
| 5,570,403 A * | 10/1996 | Yamazaki et al. | 378/5 |
| 5,628,938 A | 5/1997 | Sangeeta et al. | |
| 5,850,466 A * | 12/1998 | Schott | 382/141 |
| 6,024,898 A | 2/2000 | Steibel et al. | |
| 6,258,737 B1 | 7/2001 | Steibel et al. | |
| 6,403,158 B1 | 6/2002 | Corman | |
| 6,503,441 B2 | 1/2003 | Corman et al. | |
| 7,092,484 B1 | 8/2006 | Jensen et al. | |
| 7,586,600 B2 * | 9/2009 | Kao et al. | 356/243.1 |

(Continued)

FOREIGN PATENT DOCUMENTS

EP 1717573 A1 11/2006

OTHER PUBLICATIONS

EP 10154226.4, Search Report and Written Opinion, Aug. 24, 2010.

(Continued)

*Primary Examiner* — Tarifur Chowdhury
*Assistant Examiner* — Jonathon Cook
(74) *Attorney, Agent, or Firm* — General Electric Company; Sushupta T. Sudarshan; David J. Clement

(57) ABSTRACT

A method and system for nondestructively detecting and quantifying material anomalies within materials, including composite articles. The method entails performing a three-dimensional imaging scan technique, such as a computed tomography scan, of the material and a reference standard such that a test image of the material and a reference image of the reference standard appear in a plurality of two-dimensional scan views generated by the scan technique. The reference images are located in the scan views and normalized to determine at least an average value of the pixel data for the reference images. Values of pixel data of the test image are determined in each scan view, and then compared to the pixel data of the reference images to detect the presence of an anomaly in the test images. The detected anomaly in at least one of the test images of the scan views is then compared to a requirement standard for the material.

25 Claims, 5 Drawing Sheets

← TEST SPECIMEN

← REFERENCE STANDARD

U.S. PATENT DOCUMENTS

2004/0067316 A1     4/2004    Gray et al.
2005/0152504 A1     7/2005    Shih
2007/0291277 A1*   12/2007   Everett et al. ................. 356/497

OTHER PUBLICATIONS

Morales-Rodriguez, A.; et al., "Porosity Analysis of Long-Fiber-Reinforced Ceramic Matrix Composites Using X-Ray Tomography," journal, Mar. 1, 2009, pp. 388-390, vol. 60, No. 6, Scripta Materialia, Elsevier, Amsterdam, NL.

Mery, D., et al., "Flaw Tracking in a Sequence of Digital X-Ray Images: A New Method of Automated Quality Control of Castings," journal, Apr. 1, 2000, pp. 160-165, Technisches Messen TM, R.Oldenbourg Verlag, Munchen, DE.

Bauer, N. et al., "Determine Defects Quickly and Precisely in Plants," journal, Feb. 14, 1992, pp. 74-76, vol. 84, No. 7, Technisches Rundschau, Hallwag AG, CH.

* cited by examiner

| Standard | 4370.11 |
| --- | --- |
| Min. Pixel | 2296 |
| Max. Pixel | 5324 |
| Ave. Pixel | 4377.78 |
| StdDev. | 406.26 |

| Scope | Pixel Count | % of Slice |
| --- | --- | --- |
| Uninfiltrated | 4 | 0.01% |
| Partial Infilt. | 6184 | 8.52% |
| Total | 6188 | 8.53% |
| Slice | 72582 | 100% |

FIG.3

| Avg. Pixel | 4556.57 |
| --- | --- |
| Avg. Standard | 4373.94 |
| Avg. StdDev. | 197.84 |

| Scope | Avg. | | Max. | | Min. | Difference |
| --- | --- | --- | --- | --- | --- | --- |
| Uninfiltrated | 0.00% | 0.00% | 0.00% | 0.00% | | |
| Partial Infilt. | 0.04% | 0.13% | 0.00% | 0.13% | | |
| Total | 0.04% | 0.13% | 0.00% | 0.13% | | |

FIG.4

NONDESTRUCTIVE INSPECTION METHOD AND SYSTEM

BACKGROUND OF THE INVENTION

The present invention generally relates to nondestructive inspection methods and systems. More particularly, this invention relates to a method and system capable of nondestructively detecting and quantifying anomaly levels within materials, including composite materials such as a ceramic matrix composite (CMC) material.

Composite materials generally comprise a fiber reinforcement material embedded in a matrix material, such as a polymer or ceramic material. The reinforcement material serves as the load-bearing constituent of the composite material, while the matrix material protects the reinforcement material, maintains the orientation of its fibers, and serves to dissipate loads to the reinforcement material. In CMC materials, reinforcement materials in the form of continuous or chopped fibers (filaments) may be coated with a release agent, such as boron nitride (BN) or carbon, to form a weak interface or de-bond coating that allows for limited and controlled slip between the fibers and the ceramic matrix material. As cracks develop in the CMC material, one or more fibers bridging the crack act to redistribute the load to adjacent fibers and regions of the matrix material, thus inhibiting or at least slowing further propagation of the crack through the matrix material. From this, it should be appreciated that the presence of porosity in CMC and other composite materials not only affects the strength of the matrix material, but also the ability of the reinforcement material to carry and distribute loads within the composite material.

CMC materials reinforced with continuous fibers, often referred to as continuous fiber reinforced ceramic composites (CFCC), offer light weight, high strength, and high stiffness, and are therefore of particular interest to a variety of high-temperature load-bearing applications, including shrouds, combustor liners, vanes, blades, and other high-temperature components of gas turbine engines. The continuous fibers may be arranged to form a unidirectional array of fibers, or bundled in tows that are arranged to form a unidirectional array of tows, or bundled in tows that are woven to form a two-dimensional fabric or woven or braided to form a three-dimensional fabric. Also of particular interest to high-temperature applications are silicon-based CFCCs that employ silicon carbide (SiC) as the matrix and/or reinforcement material. A notable example of a silicon-based CFCC has been developed by the General Electric Company under the name HiPerComp®, and contains continuous silicon carbide fibers in a matrix of silicon carbide and elemental silicon or a silicon alloy. Particular examples of SiC/Si—SiC (fiber/matrix) CFCC materials and processes are disclosed in commonly-assigned U.S. Pat. Nos. 5,015,540, 5,330,854, 5,336,350, 5,628,938, 6,024,898, 6,258,737, 6,403,158, and 6,503,441, and commonly-assigned U.S. Patent Application Publication No. 2004/0067316. One such process is known as "prepreg" melt-infiltration (MI), which in general terms entails the fabrication of CMCs using multiple prepreg layers, each in the form of a tape-like structure comprising the desired reinforcement material, a precursor of the CMC matrix material, and one or more binders. Multiple prepreg layers are stacked and debulked to form a laminate preform, a process referred to as "lay-up," followed by curing while subjected to applied pressure and an elevated temperature, such as in an autoclave. The laminate preform is then heated (fired) in a vacuum or an inert atmosphere to convert the precursor to the desired ceramic material, decompose the binder, and produce a porous preform that can then be melt infiltrated with molten silicon or another suitable infiltrant during the same or subsequent heating step. The infiltrant fills the porosity and, depending on its composition, may react to form additional matrix material.

As previously noted, the presence of any residual porosity is an important issue since it can have a significant affect on the properties of a CMC material. It should be well understood that other types of void defects, such as delaminations, are also detrimental to the strength of CMCs and other composite materials. Consequently, various nondestructive examination (NDE) and nondestructive test (NDT) techniques have been considered for determining void levels in CMC materials, including but not limited to immediately following a melt infiltration process. In addition to being sensitive to the volumetric void level, the properties of a CMC material can differ depending on the type of void, for example, a discrete anomaly, generalized porosity, or delamination. Consequently, NDT methods capable of detecting and characterizing void conditions are needed. Current NDT methods for composites include radiography (RT), ultrasonic (UT), computed tomography (CT) scanning, and infrared (IR) thermography such as flash infrared thermography (Flash IR) and through transmission thermography (TT IR). Results of these NDT methods routinely require the analysis of a trained technician.

In practice, Flash IR imaging techniques have been found to work well for near-surface indications with high levels of porosity. However, Flash IR produces a two-dimensional (2-D) image, and the detection capability of Flash IR decreases as part thickness increases and as the pore size and percentage of porosity decrease. Though TT IR overcomes some of the limitations of Flash IR, the result is still a 2-D image. As a result, though an estimate of percent porosity can be made from the IR data, it can be difficult to determine the size (depth and thickness) of the porosity or other void indication. Without such information, the full impact of a void on material properties cannot be known.

UT and RT (X-ray) techniques have certain advantages and disadvantages over IR when used to inspect various composite material systems, though both are 2-D imaging technologies and therefore share the same limitation as IR in terms of being incapable of fully characterizing the depth and thickness of a detected void condition. In contrast, CT scanning generates a full three-dimensional (3-D) image of a test specimen by utilizing digital geometry processing of a series of two-dimensional X-ray images taken around a single axis of rotation. However, the generated 3-D data set is very large and must be reviewed by a trained technician. To fully assess the percentage of porosity, a technician would require hours to evaluate the CT data set and characterize the porosity indications.

In view of the above, it would be desirable if a fast and reliable nondestructive test method existed for detecting and characterizing void regions within a composite material to ensure material properties.

BRIEF SUMMARY OF THE INVENTION

The present invention provides a method and system for nondestructively inspecting materials, including composite materials comprising fibrous reinforcement materials in a matrix material, as well as monolith articles including castings, moldings, forgings, extrusions and other materials that may contain non-surface related material anomalies. The invention more preferably provides for the detection and quantifying of anomalies (for example, porosity, delamination defects and other voids) in monolithic and composite materials. Notable but nonlimiting examples of materials that can be nondestructively inspected include polymer matrix composite (PMC) and ceramic matrix composite (CMC) articles comprising a fibrous reinforcement material in a matrix material, such as CMC articles suitable for use in high-temperature load-bearing applications, including shrouds, combustor liners, vanes, blades, and other high-temperature components of gas turbine engines.

According to a first aspect of the invention, the method entails the use of a reference standard having a known density. A three-dimensional imaging scan technique, such as a computed tomography scan, is performed of the material and the reference standard such that a test image of the material and a reference image of the reference standard appear in a plurality of two-dimensional scan views generated by the scan technique, and the reference images and the test images comprise pixel data corresponding to amounts of scan energies absorbed at two-dimensional cross-sections of the reference standard and the material. The reference images of the reference standard are located in the scan views, and then normalized to determine at least an average value of the pixel data for the reference images. The values are determined for the pixel data of the test image in each scan view, and then the values of the pixel data of the test image in each of the scan views are compared to at least the average value of the pixel data of the reference images to detect the presence of an anomaly in the test images. The detected anomaly in at least one of the test images of the scan views is then compared to a requirement standard for the material.

According to a second aspect of the invention, the system is preferably adapted to perform the method described above. In this regard, the system entails the reference standard, means for performing the three-dimensional imaging scan technique of the material and the reference standard, means for locating the reference images of the reference standard in the two-dimensional scan views, means for normalizing the reference images of the reference standard in the scan views to determine at least an average value of the pixel data for the reference images, means for determining values of the pixel data of the test image in each of the scan views, means for comparing the values of the pixel data of the test image in each of the scan views to at least the average value of the pixel data of the reference images to detect the presence of an anomaly, and means for comparing the detected anomaly in at least one of the test images of the scan views to a requirement standard for the material.

From the above, it can be appreciated that the method and system of this invention are adapted to perform a nondestructive examination of a composite article or other scannable material, and therefore can be performed on production components that will later be placed in service. A technical effect of the invention is the ability to detect the presence of anomalies (including porosity and other voids) throughout a material. Preferred technical effects of the invention include the ability to qualify and preferably quantify anomalies, including characterization of the size (depth and thickness) of a detected void region, so that the properties of the material can be more fully assessed.

Other aspects and advantages of this invention will be better appreciated from the following detailed description.

BRIEF DESCRIPTION OF THE DRAWINGS

FIG. 3 represents a software-generated screen displaying statistics based on pixel data obtained from a single CT image of a test specimen.

FIG. 4 represents a software-generated screen displaying bulk statistics based on pixel data obtained and compiled from all CT images of a test specimen.

DETAILED DESCRIPTION OF THE INVENTION

Figure 7:
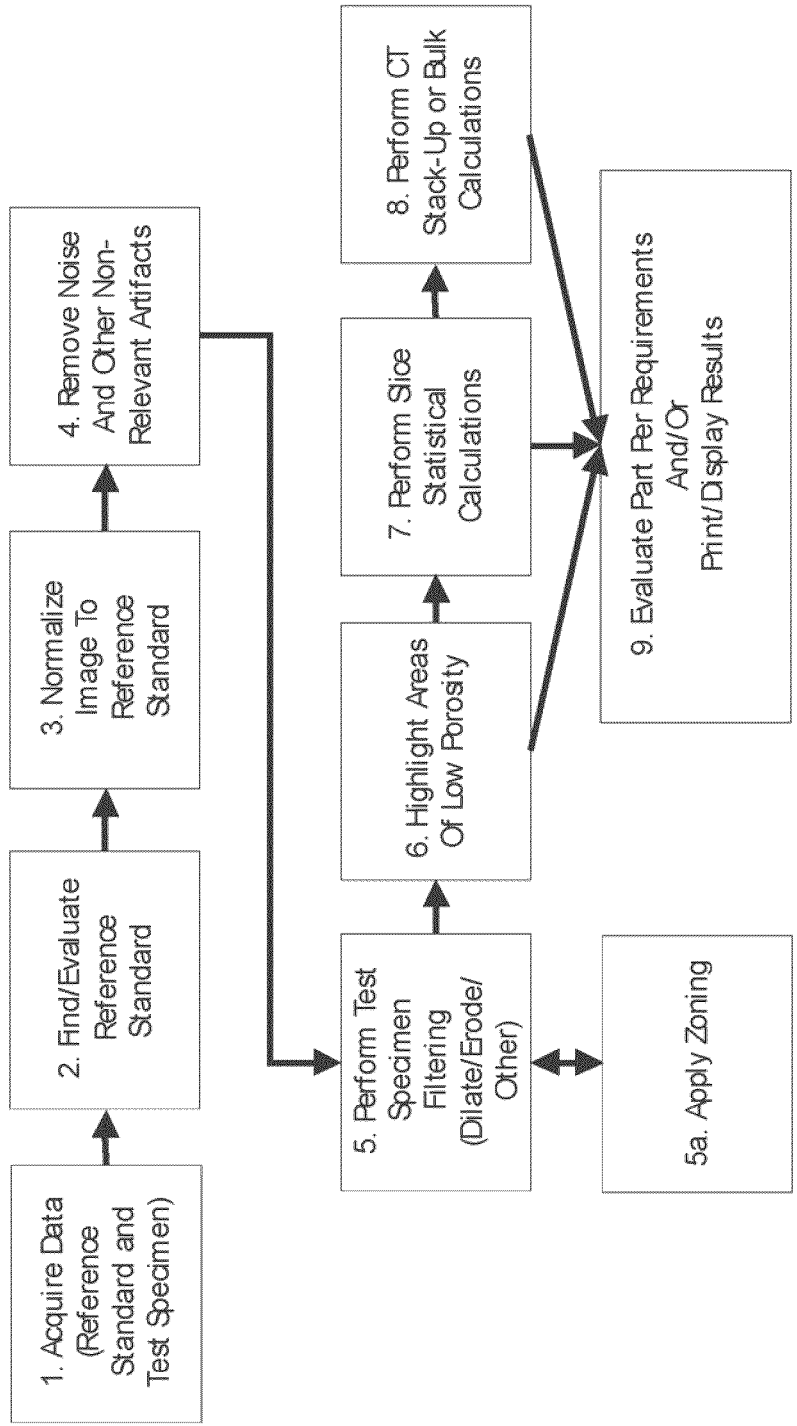
FIG. 7 represents a process flowchart showing steps carried out during a void detection process in accordance with a preferred embodiment of this invention.

The following describes a nondestructive test (NDT) method and system for detecting material anomalies in materials, including voids in monolith and composite articles, and qualifying and quantifying levels of such material anomalies using a 3-D imaging technique that generates a full 3-D image by utilizing digital geometry processing of a series of two-dimensional images, each of which contains pixel data that correspond to amounts of scanning energy absorbed by a material that directly corresponds to densities of the material. A preferred 3-D imaging technique is believed to utilize CT scanning technology, though other 3-D imaging techniques are also within the scope of the invention, including magnetic resonance imaging (MRI) and ultrasonic (UT) scanning technologies. A process flowchart showing steps that may be carried out using this method is represented in FIG. 7. According to a preferred aspect of the invention, the method and system obtain numerous two-dimensional scan images of a test specimen and a reference standard, providing a comparative basis from which an analytical assessment can be performed to identify voids and quantify void levels within the test specimen.

The method and system will be particularly described in reference to CMC articles, including CFCC articles, nonlimiting examples of which include CMC materials that contain silicon carbide as the reinforcement and/or matrix material. However, other CMC materials as well as other composite materials (for example, polymer matrix composite (PMC) materials) are also within the scope of the invention, including SiC fibers and other fiber materials that have been used to reinforce a variety of matrix materials, including SiC, titanium carbide (TiC), silicon nitride ($Si_3N_4$), and alumina ($Al_2O_3$). The invention is also particularly applicable to CMC materials produced by a process that includes a melt infiltration step, as reported in U.S. Pat. Nos. 5,015,540, 5,330,854, 5,336,350, 5,628,938, 6,024,898, 6,258,737, 6,403,158, and 6,503,441, and commonly-assigned U.S. Patent Application Publication No. 2004/0067316, though other processes for producing composite articles are also within the scope of the invention. Finally, while various applications are foreseeable for composite materials inspected in the manner described below, particular applications of interest include components of gas turbine engines, such as combustor liners, blades, vanes and shrouds of gas turbines.

Figure 1:
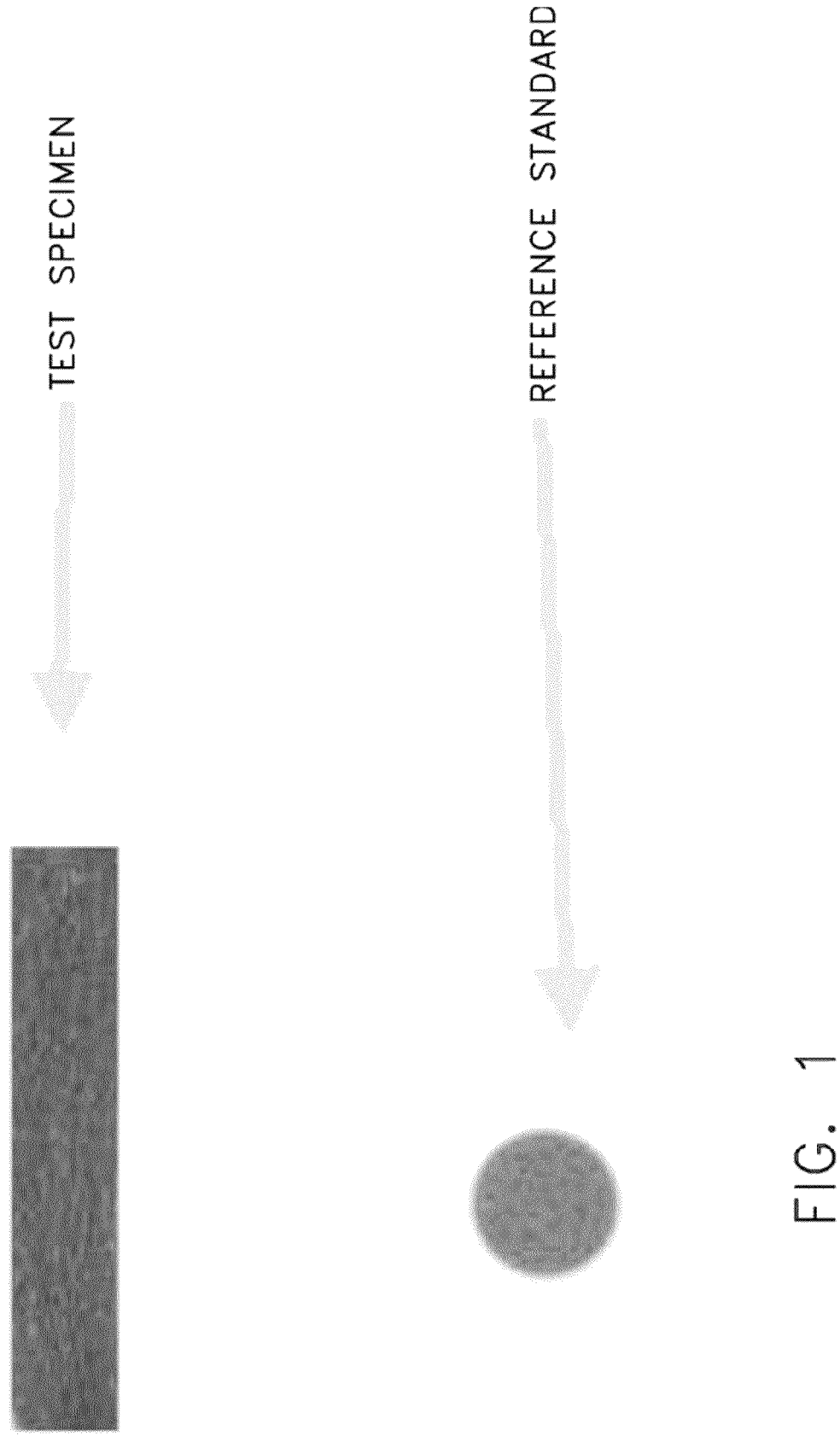
FIG. 1 is an image obtained by performing a computed tomography (CT) scan of a test specimen and a reference standard in accordance with a preferred embodiment of this invention.

FIG. 1 shows a two-dimensional digital image obtained by performing a CT scan of a test specimen and a reference standard having a known density. The test specimen is a vane of a type used in the turbine section of a gas turbine engine, and the reference standard is an aluminum cylinder. Other materials and shapes for the reference standard are foreseeable and could be used. Generally, it is believed that relatively simple cross-sectional shapes, such as circular, square, rectangular, etc., are preferred for the reference standard due to their ease of being found and evaluated in a scan. In the particular CT scan shown, the reference standard has a density of about ninety percent of the ideal density for the test standard. To obtain the visual digital image in FIG. 1, the test specimen and reference standard were fixtured so that both appear in each of a plurality of two-dimensional CT scan views of the test specimen. The CT equipment used to generate the CT scan of FIG. 1 and other CT images shown in the drawings was a 3-D x-ray imaging (3DXR) system manufactured by the General Electric Company. FIG. 1 presents one of a large number of two-dimensional scan views (slices) that were generated of the same test specimen and reference standard. Together, these scan views will be referred to as a stack-up of CT slices, whose individual slices portray images at parallel two-dimensional cross-sections of the test specimen and reference standard. The images can be spaced apart any distance that will provide a desired level of inspection, for example, a fraction of a millimeter or more. Within each CT view, pixel data correspond to the amounts of X-rays absorbed at one of the cross-sections of the test specimen and reference standard, and directly correspond to densities of the materials within each CT view. From these CT views, an automatic imaging algorithm processes normalized CT pixel value data to produce meaningful statistics that detect voids within the test specimen, as well as quantify voids within the test specimen. Accordingly, the method of this invention involves an imaging routine that locates the reference standard and the test specimen in each CT view of the stack-up, and measures and analyzes pixel data obtained from the image of the reference standard (the reference image) and the image of test specimen (the test image) within each CT view.

Standard image processing techniques can be employed to obtain pixel values from the reference image in each CT view. The reference image pixel data can then be statistically analyzed to obtain an average value and standard deviation for each CT view. A hit-or-miss imaging algorithm of a type known in the art can be useful to locate shapes of certain sizes, such as the test specimen and reference standard seen in FIG. 1. A binary image (mask) of the location of the reference standard can be created using this technique and then applied to the original CT image to obtain the pixel values of the reference image. Though the general location of the reference standard is known, a margin of error may be taken into account due to fixturing and mounting repeatability. Nonetheless, knowledge of the general location of the reference standard allows the search area for the reference image to be narrowed to save on processing time.

Based upon the statistics acquired from the reference image, the entire CT view can be scaled in order to normalize the test specimen image. Each set of CT data acquired from the test specimen image is scaled relative to the CT data acquired from the reference standard image in the same CT view. The scale is preferably based on a correlation between the density of the reference standard and the desired density of the test specimen.

The process further involves acquiring pixel data from the test image in each CT view. To do so, the imaging routine locates the test specimen in the CT image, and preferably eliminates background noise and/or fixturing that does not need to be evaluated. This step may include the application of a threshold or band-pass filter to eliminate background noise and fixturing values in the CT image, in which case these values simply fall below the chosen threshold or band-pass region.

After removal of background noise from its CT test image, the test specimen within the image is preferably subjected to a dilate and erode filter technique to create a mask that defines an area encompassed by the test specimen and to be subjected to analysis. A dilate filter is preferably employed so that areas that are physically within the test specimen but have a value comparable to that of background noise or fixturing in the test image can still be evaluated. A side effect of using a dilate filter is artificial growth of the test image boundaries. Consequently, an erode filter is preferably employed to trim or cut back on the artificial growth of the test image area, preferably without removing any portion of the test image from the CT image. The amount or size of the resulting dilate or erode element will typically be specific to the particular test specimen and depend largely on the quality of the specimen. A direct relationship exists between the size of void regions to be detected and the size of the element needed to correct the test image of the test specimen.

As a result of the above-noted threshold, band-pass and/or filtering techniques, pixel values accurately indicative of the test specimen can be obtained and normalized to the pixel data of the reference image. As with the reference standard, known image processing techniques can be applied to the test image to automatically evaluate each CT pixel value. It is believed that in many applications, a threshold level will be useful to specifically identify areas within the test specimen below a certain density level. According to a preferred aspect of the invention, this threshold level can be set relative to the average pixel value of the reference image and can be adjusted to accommodate the requirements of a particular test specimen. As a nonlimiting example, the threshold level can be set to a value of 50% of the average pixel value calculated for the reference image. Because of prior knowledge of the density of the standard reference, the threshold level can be used to qualitatively assess density levels within the test specimen.

Figure 2:
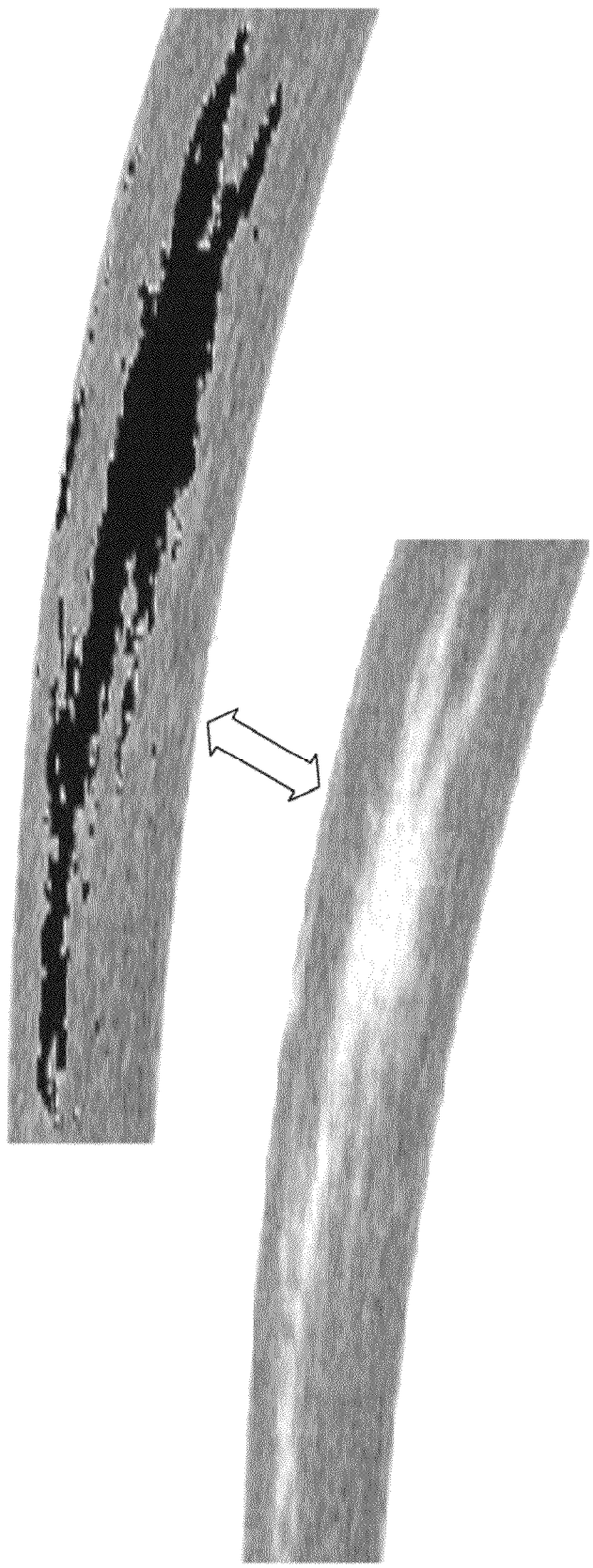
FIG. 2 contains a first magnified image of a portion of a test specimen taken from a CT scan similar to FIG. 1 and showing regions of low density in the test specimen, and a second magnified image that depicts the effect of highlighting the low density regions of the first magnified image.

FIG. 2 contains a digital image showing a portion of a test image whose pixel data have been processed to indicate regions of the test specimen that fall below a predetermined threshold level, and contains a second digital image showing the effect of visually highlighting the low density regions of the first image to assist a technician performing the analysis. The highlighting effect can be achieved in a number of ways known in the art of standard image processing techniques. For example, in FIG. 2 a binary mask has been applied to the first image to generate the second image. By highlighting low-density pixel values, it becomes clearer to the technician as to where low density (porous) regions exist within the test specimen, and facilities qualitative and quantitative analysis of the size and location of the void within the test specimen. Alternatively or in addition, imaging techniques and software can be used to statistically analyze pixel data obtained from the test image and create a summary of pixel data statistics. Nonlimiting examples of such statistics include the average and/or mean pixel value, standard deviation value, minimum and maximum pixel values, and the amount of low density regions (below a set threshold) as a percentage of the cross-section of the test specimen analyzed in each CT image. FIG. 3 represents a software-generated screen displaying statistics based on pixel data obtained from a single CT test image of a test specimen. Included in the statistical display are the average pixel value, standard deviation value, minimum and maximum pixel values, and percentage of the specimen that has low density regions based on differing levels or severity of porosity for the specimen ("Uninfiltrated," "Partial Infilt.," and "Total") for the test specimen. For comparison, the screen shown in FIG. 3 also displays the average pixel value ("Standard") for the reference standard that was scanned with the test specimen.

For some applications, the test specimen may have multiple inspection limits for porosity (or other void content) based on attributes such as area, volume, length, density, location or proximity to other porosity regions. For this reason, the method can further include a routine to segregate different regions or zones of the test specimen by applying registration routines specific to the particular test specimen and zones within the specimen that are of particular interest. The routine can then calculate any desired statistics based on pixel data obtained from these zones, and then analyze and compare the data and statistics relative to the inspection limits individually established for each zone.

Figure 5:
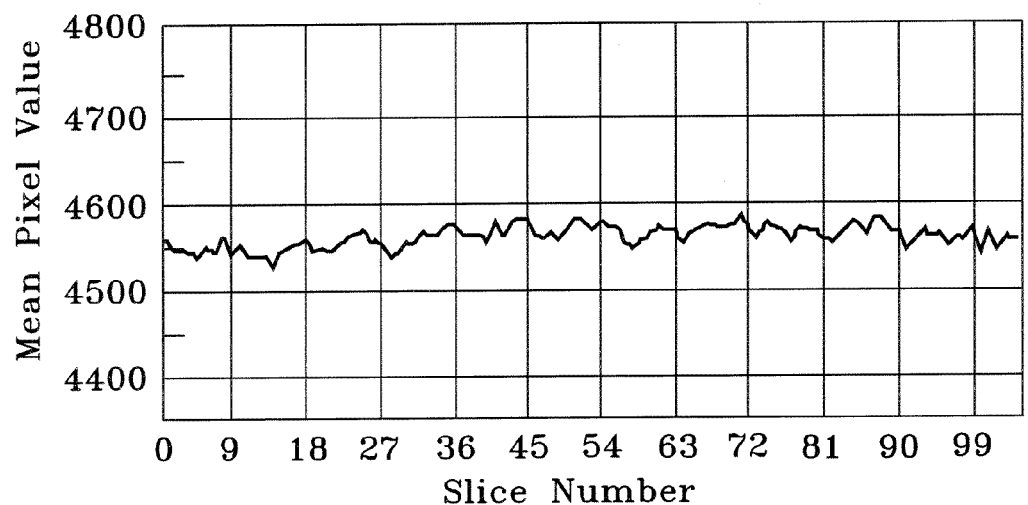
FIG. 5 represents a plot of mean pixel values based on pixel data obtained and compiled from all CT images of a test specimen.
Figure 6:
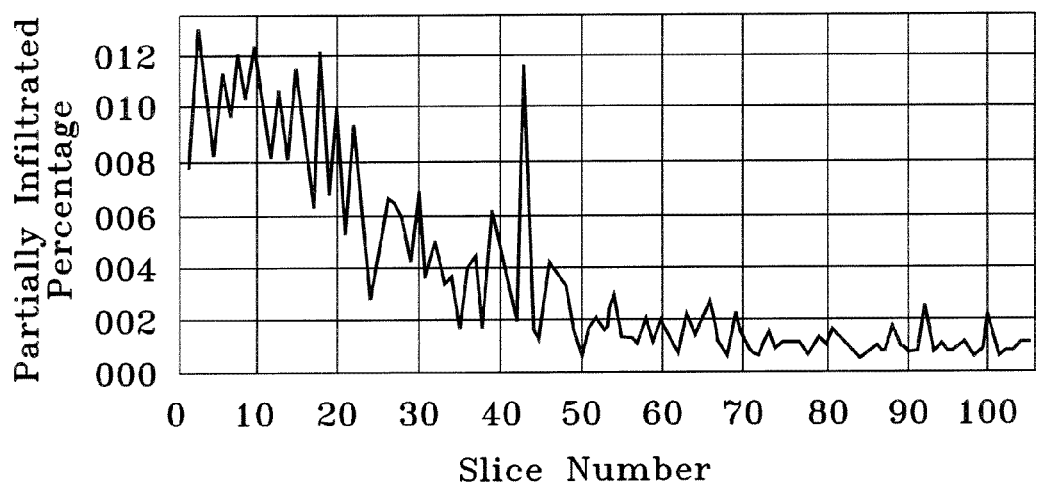
FIG. 6 represents a plot of the cross-sectional area percentage identified as "low density" based on pixel data obtained and compiled from all CT images of a test specimen.

The routine described above for each CT image is preferably performed for each image in the stack-up of CT images, enabling the creation of statistical summaries, plots and charts that can highlight areas of interest to a technician. Such processing of statistics for an entire test specimen is referred to herein as bulk processing. An example of a bulk statistical summary is represented in FIG. 4, which shows statistical data, including average, maximum, and minimum pixel values and the percentage of low density regions (e.g., below a set threshold) for an entire test specimen. Examples of bulk statistical plots for mean pixel value and low density percentage of an entire specimen are represented in FIGS. 5 and 6, respectively. The data displayed by the screen of FIG. 4 and the data plotted in the graphs of FIGS. 5 and 6 provide both numerical (quantitative) and visual (qualitative) comparisons to the reference image, whose average pixel value is displayed in FIG. 4 and, if so desired, could be plotted in FIG. 5.

From the forgoing, it can be appreciated that the detection and characterization of anomalies within materials, including void regions within composite materials, may be obtained by performing a three-dimensional imaging scan technique of the test specimen and a reference standard so that a test image and a reference image appear in the scan views. The presence of images of both the reference standard and test specimen in each of a plurality of scan views allows for the generation and comparison of data to detect the presence of anomalies throughout the test specimen. Furthermore, the method described above provides numerous time-saving opportunities, due in part to the capability for automatic normalization and scaling of data and highlighting of identified low-density regions in a test specimen. Without such capabilities, analysis of the CT images would be subject to changes in contrast and operator judgment as to whether a region of interest is actually a porous (low density) region or merely appears to be porous. Automatic processing of test image data and the ability for zone-specific and/or bulk analysis of a test specimen further assists a technician to quickly assess whether a test specimen meets acceptance design criteria based on void/porosity content and properties that depend on density. Advantageously, a system capable of carrying out the steps described above can be adapted from pre-existing CT scanning equipment and pre-existing imaging equipment using known imaging techniques, which are then appropriately controlled with computer-based software to perform the imaging algorithms discussed above, including algorithms for locating the test and reference images in the scan views, normalizing and determining pixel data values in the images, and comparing pixel data values to identify and quantify voids in the test specimen. Finally, the operation of the equipment and the method as a whole can be tailored to optimize the speed of the NDT analysis.

While the invention has been described in terms of particular embodiments, it is apparent that other forms could be adopted by one skilled in the art. Therefore, the scope of the invention is to be limited only by the following claims.

The invention claimed is:

1. A nondestructive method of inspecting a material, the method comprising the steps of:
   providing a reference standard having a known density;
   performing a three-dimensional imaging scan technique on the material and the reference standard such that a test image of the material and a reference image of the reference standard appear together in each of a plurality of parallel two-dimensional scan views generated by the three-dimensional imaging scan technique, the reference images and the test images comprising pixel data corresponding to amounts of scan energies absorbed at each of a plurality of parallel two-dimensional cross-sections of the reference standard and the material;
   locating the reference images of the reference standard in the scan views;
   normalizing the reference images of the reference standard in the scan views to determine at least an average value of the pixel data for the reference images;
   determining values of the pixel data of the test image in each of the scan views;
   comparing the values of the pixel data of the test image in each of the scan views to at least the average value of the pixel data of the reference images to detect the presence of an anomaly in the test image in each of the scan views; and
   comparing the detected anomaly in at least one of the test images of the scan views to a requirement standard for the material.

2. The nondestructive method according to claim 1, further comprising the step of removing background noise from the test images of the material prior to comparing the values of the pixel data of the test image in each of the scan views to at least the average value of the pixel data of the reference images.

3. The nondestructive method according to claim 1, further comprising the step of filtering the test images to mask areas of the scan views outside the cross-sections of the material prior to comparing the values of the pixel data of the test image in each of the scan views to at least the average value of the pixel data of the reference images.

4. The nondestructive method according to claim 1, further comprising the steps of:
   displaying the test images as digital visual test images; and
   visually highlighting areas of the digital visual test images corresponding to the presence of the anomaly within the material that exceeds a predetermined threshold.

5. The nondestructive method according to claim 1, wherein the step of comparing the detected anomaly comprises performing a bulk assessment by comparing the detected anomaly in a plurality of the test images of the scan views to a bulk requirement standard for the material.

6. The nondestructive method according to claim 1, wherein the material is a composite article comprising a fibrous reinforcement material in a matrix material.

7. The nondestructive method according to claim 6, wherein the composite article is a ceramic matrix composite material.

8. The nondestructive method according to claim 7, wherein the ceramic matrix composite material is produced by a melt infiltration process.

9. The nondestructive method according to claim 7, wherein the ceramic matrix composite article is a component of a gas turbine engine.

10. A nondestructive method of inspecting a composite article comprising a fibrous reinforcement material in a matrix material, the method comprising the steps of:
providing a reference standard having a known density;
performing a computed tomography scan of the composite article and the reference standard such that a test image of the composite article and a reference image of the reference standard appear together in each of a plurality of parallel scan views generated by the computed tomography scan, the reference images and the test images comprising pixel data corresponding to amounts of X-rays absorbed at each of a plurality of parallel two-dimensional cross-sections of the reference standard and the composite article;
locating the reference images of the reference standard in the scan views;
normalizing the reference images of the reference standard in the scan views to determine at least an average value of the pixel data for the reference images;
removing background noise from the test images of the composite article;
filtering the test images to mask areas of the scan views outside the cross-sections of the composite article;
determining values of the pixel data of the test image in each of the scan views;
comparing the values of the pixel data of the test image in each of the scan views to at least the average value of the pixel data of the reference images to detect the presence of a void in the test image in each of the scan views; and
performing a bulk assessment by comparing the detected void in a plurality of the test images of the scan views to a bulk requirement standard for the composite article.

11. The nondestructive method according to claim 10, wherein the composite article is a ceramic matrix composite material.

12. The nondestructive method according to claim 11, wherein the ceramic matrix composite material is produced by a melt infiltration process.

13. The nondestructive method according to claim 11, wherein at least one of the fibrous reinforcement material and the matrix material of the ceramic matrix composite article comprises silicon carbide.

14. The nondestructive method according to claim 11, wherein the ceramic matrix composite article is a component of a gas turbine engine.

15. A system for nondestructively inspecting a material, the system comprising;
a reference standard having a known density;
means for performing a three-dimensional imaging scan technique on the material and the reference standard such that a test image of the material and a reference image of the reference standard appear together in each of a plurality of parallel two-dimensional scan views generated by the three-dimensional imaging scan technique, the reference images and the test images comprising pixel data corresponding to amounts of scan energies absorbed at each of a plurality of parallel two-dimensional cross-sections of the reference standard and the material;
means for locating the reference images of the reference standard in the scan views;
means for normalizing the reference images of the reference standard in the scan views to determine at least an average value of the pixel data for the reference images;
means for determining values of the pixel data of the test image in each of the scan views;
means for comparing the values of the pixel data of the test image in each of the scan views to at least the average value of the pixel data of the reference images to detect the presence of an anomaly in the test image in each of the scan views; and
means for comparing the detected anomaly in at least one of the test images of the scan views to a requirement standard for the material.

16. The system according to claim 15, further comprising means for removing background noise from the test images of the material prior to comparing the values of the pixel data of the test image in each of the scan views to at least the average value of the pixel data of the reference images.

17. The system according to claim 15, further comprising means for filtering the test images to mask areas of the scan views outside the cross-sections of the material prior to comparing the values of the pixel data of the test image in each of the scan views to at least the average value of the pixel data of the reference images.

18. The system according to claim 15, further comprising:
means for displaying the test images as digital visual test images; and
means for visually highlighting areas of the digital visual test images corresponding to the presence of the anomaly within the material that exceeds a predetermined threshold.

19. The system according to claim 15, wherein the means for comparing the detected anomaly comprises means for performing a bulk assessment by comparing the detected anomaly in a plurality of the test images of the scan views to a bulk requirement standard for the material.

20. The system according to claim 15, wherein the material is a ceramic matrix composite material.

21. The nondestructive method according to claim 1, wherein the material is a monolith article selected from the group consisting of castings, moldings, forgings, and extrusions.

22. The nondestructive method according to claim 6, wherein the composite article is a polymer matrix composite material.

23. The nondestructive method according to claim 10, wherein the composite article is a polymer matrix composite material.

24. The system according to claim 15, wherein the material is a monolith article selected from the group consisting of castings, moldings, forgings, and extrusions.

25. The system according to claim 15, wherein the material is a polymer matrix composite material.

* * * * *